United States Patent
Facchetti et al.

(10) Patent No.: US 9,812,645 B2
(45) Date of Patent: Nov. 7, 2017

(54) PERYLENE-BASED SEMICONDUCTORS

(71) Applicant: Flexterra, Inc., Skokie, IL (US)

(72) Inventors: Antonio Facchetti, Chicago, IL (US);
Mitchell Denti, Chicago, IL (US)

(73) Assignee: Flexterra, Inc., Skokie, IL (US)

( * ) Notice: Subject to any disclaimer, the term of this patent is extended or adjusted under 35 U.S.C. 154(b) by 0 days.

(21) Appl. No.: 15/043,956

(22) Filed: Feb. 15, 2016

(65) Prior Publication Data

US 2016/0240789 A1     Aug. 18, 2016

Related U.S. Application Data

(60) Provisional application No. 62/116,369, filed on Feb. 13, 2015.

(51) Int. Cl.
| | | |
|---|---|---|
| *C07D 487/06* | (2006.01) | |
| *H01L 51/00* | (2006.01) | |
| *H01L 51/05* | (2006.01) | |
| *H01L 51/42* | (2006.01) | |
| *H01L 51/50* | (2006.01) | |

(52) U.S. Cl.
CPC ........ *H01L 51/0053* (2013.01); *C07D 487/06* (2013.01); *H01L 51/0558* (2013.01); *H01L 51/4253* (2013.01); *H01L 51/5012* (2013.01)

(58) Field of Classification Search
CPC .................. C07D 487/06; H01L 51/0053
See application file for complete search history.

(56) References Cited

U.S. PATENT DOCUMENTS

| | | | |
|---|---|---|---|
| 5,886,183 A | 3/1999 | Langhals et al. | 546/62 |
| 6,143,890 A | 11/2000 | Langhals et al. | 544/233 |
| 7,452,385 B2 | 11/2008 | Speckbacher et al. | 8/405 |
| 2005/0176970 A1 | 8/2005 | Marks et al. | 546/37 |
| 2010/0202984 A1 | 8/2010 | Langhals et al. | 424/59 |
| 2010/0319778 A1 | 12/2010 | Kastler et al. | 136/263 |
| 2011/0213117 A1 | 9/2011 | Facchetti | 528/321 |

*Primary Examiner* — Shawquia Jackson
(74) *Attorney, Agent, or Firm* — McDonnell Boehnen Hulbert & Berghoff LLP

(57) ABSTRACT

The present invention relates to new semiconductor materials prepared from perylene-based compounds. Such compounds can exhibit high carrier mobility and/or good current modulation characteristics. In addition, the compounds of the present teachings can possess certain processing advantages such as solution-processability and/or good stability at ambient conditions.

20 Claims, 2 Drawing Sheets

PERYLENE-BASED SEMICONDUCTORS

CROSS-REFERENCE TO RELATED APPLICATIONS

This application claims priority to and the benefit of U.S. Provisional Patent Application Ser. No. 62/116,369 filed on Feb. 13, 2015, the disclosure of which is incorporated by reference herein in its entirety.

BACKGROUND

Organic optoelectronic devices such as organic thin film transistors (OTFTs), organic light emitting diodes (OLEDs), printable circuits, organic photovoltaic devices, capacitors and sensors are fabricated using small molecule or polymeric semiconductors as their active components. To achieve high-speed performance and efficient operation, it is desirable that both the p-type and n-type semiconductor materials in these organic semiconductor-based devices exhibit high charge carrier mobility (μ) and stability under ambient conditions, and can be processed in a cost-effective manner.

Accordingly, the art continues to desire new organic semiconductors, particularly those having good stability, processing properties, and/or charge transport characteristics in ambient conditions.

SUMMARY

In light of the foregoing, the present teachings provide perylene-based semiconducting compounds that can exhibit properties such as good charge transport characteristics under ambient conditions, chemical stability, low-temperature processability, large solubility in common solvents, and processing versatility. As a result, field effect devices such as thin film transistors that incorporate the present compounds as the semiconductor layer can have high performance under ambient conditions, for example, demonstrating one or more of large electron mobilities, low threshold voltages, and high current on-off ratios.

In various embodiments, the present teachings provide compounds of formula I:

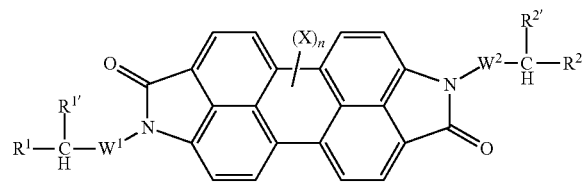

wherein $W^1$, $W^2$, X, $R^1$, $R^{1'}$, $R^2$, $R^{2'}$, and n are as defined herein.

The present teachings also provide methods of preparing semiconductor materials, as well as various compositions, composites, and devices that incorporate the compounds and semiconductor materials disclosed herein.

The foregoing as well as other features and advantages of the present teachings will be more fully understood from the following figures, description, examples, and claims.

BRIEF DESCRIPTION OF THE DRAWINGS

It should be understood that the drawings described below are for illustration purpose only. The drawings are not necessarily to scale, with emphasis generally being placed upon illustrating the principles of the present teachings. The drawings are not intended to limit the scope of the present teachings in any way.

DETAILED DESCRIPTION

Figure 1:
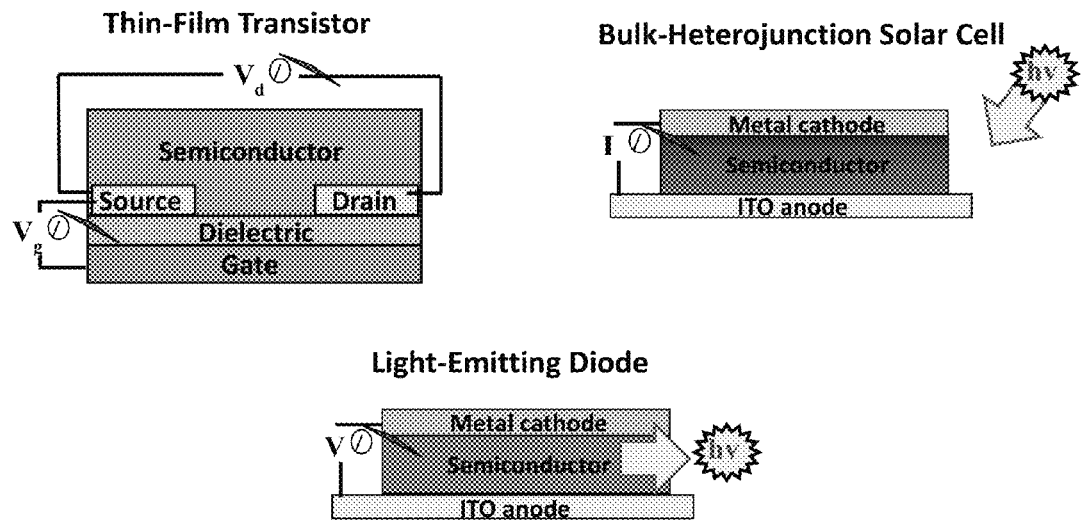
FIG. 1 illustrates the device structures of a thin-film transistor, a bulk-heterojunction solar cell, and a light-emitting diode.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula $-C_sH_{2s+1-t}X^0{}_t$, where $X^0$, at each occurrence, is F, Cl, Br or I, s is an integer in the range of 1 to 40, and t is an integer in the range of 1 to 81, provided that t is less than or equal to 2s+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxy, hexoxy groups, and the like. The alkyl group in the —O-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

Compounds of the present teachings can include a "divalent group" defined herein as a linking group capable of forming a covalent bond with two other moieties. For example, compounds of the present teachings can include a divalent $C_{1-20}$ alkyl group (e.g., a methylene group), a divalent $C_{2-20}$ alkenyl group (e.g., a vinylyl group), a divalent $C_{6-14}$ aryl group (e.g., a phenylyl group), and/or a divalent 5-14 membered heteroaryl group (e.g., a thienylyl group).

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group." In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), $-NO_2$, $-CN$, $-NC$, $-S(R^0)_2{}^+$, $-N(R^0)_3{}^+$, $-SO_3H$, $-SO_2R^0$, $-SO_3R^0$, $-SO_2NHR^0$, $-SO_2N(R^0)_2$, $-COOH$, $-COR^0$, $-COOR^0$, $-CONHR^0$, $-CON(R^0)_2$, $C_{1-40}$ haloalkyl groups, $C_{6-14}$ aryl groups, and 5-14 membered electron-poor heteroaryl groups; where $R^0$ is a $C_{1-40}$ alkyl group, a $C_{2-40}$ alkenyl group, a $C_{2-40}$ alkynyl group, a $C_{1-40}$ haloalkyl group, a $C_{1-40}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted as described herein.

It should be understood that the term "electron-donating group" can be used synonymously herein with "electron donor." In particular, an "electron-donating group" or an "electron-donor" refers to a functional group that donates electrons to a neighboring atom more than a hydrogen atom would if it occupied the same position in a molecule. Examples of electron-donating groups include —OH, $-OR^0$, $-NH_2$, $-NHR^0$, $-N(R^0)_2$, 5-14 membered electron-rich heteroaryl groups, $C_{1-40}$ alkyl groups, $C_{2-40}$ alkenyl groups, $C_{2-40}$ alkynyl groups, $C_{1-40}$ alkoxy groups, where $R^0$ is a $C_{1-40}$ alkyl group, a $C_{2-40}$ alkenyl group, a $C_{2-40}$ alkynyl group, a $C_{6-14}$ aryl group, or a $C_{3-14}$ cycloalkyl group.

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

It is specifically contemplated that the depiction of one stereoisomer includes any other stereoisomer and any stereoisomeric mixtures unless specifically stated otherwise.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

As used herein, a "p-type semiconductor material" or a "p-type semiconductor" refers to a semiconductor material having holes as the majority current carriers. In some embodiments, when a p-type semiconductor material is deposited on a substrate, it can provide a hole mobility in excess of about $10^{-5}$ cm$^2$/Vs. In the case of field-effect devices, a p-type semiconductor can also exhibit a current on/off ratio of greater than about 10.

As used herein, an "n-type semiconductor material" or an "n-type semiconductor" refers to a semiconductor material having electrons as the majority current carriers. In some embodiments, when an n-type semiconductor material is deposited on a substrate, it can provide an electron mobility in excess of about $10^{-5}$ cm$^2$/Vs. In the case of field-effect devices, an n-type semiconductor can also exhibit a current on/off ratio of greater than about 10.

As used herein, "mobility" refers to a measure of the velocity with which charge carriers, for example, holes (or units of positive charge) in the case of a p-type semiconductor material and electrons in the case of an n-type semiconductor material, move through the material under the influence of an electric field. This parameter, which depends on the device architecture, can be measured using a field-effect device or space-charge limited current measurements.

Throughout the specification, structures may or may not be presented with chemical names. Where any question arises as to nomenclature, the structure prevails.

The present teachings provide various semiconducting small molecule compounds as well as compositions and organic semiconductor materials prepared from such compounds and compositions. The organic semiconductor materials disclosed herein can exhibit useful electrical properties and can be solution-processable, e.g., spin-coatable and printable. In various embodiments, these materials can be considered p-type semiconductors. The semiconductor materials disclosed herein can be used to fabricate various organic electronic articles, structures and devices, including field-effect transistors, unipolar circuitries, complementary circuitries, and photovoltaic devices.

More specifically, the present teachings relate to compounds having formula I-1:

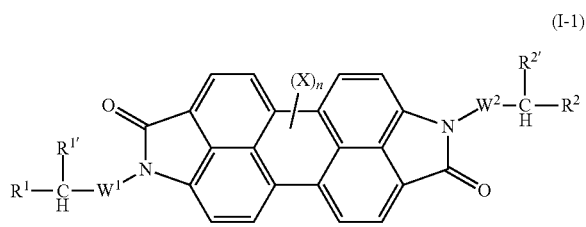

(I-1)

wherein:

$W^1$ and $W^2$ independently are selected from —$(CR^aR^b)_m$—, —$(SiR^cR^d)$—, and Ar;

X, at each occurrence, independently is selected from halogen, CN, and $OR^e$;

Ar is a divalent aryl or heteroaryl group selected from phenyl, thienyl, and furyl;

$R^a$ and $R^b$ independently are selected from H, a $C_{1-20}$ alkyl group, a $C_{2-20}$ alkenyl group, and a $C_{1-20}$ haloalkyl group;

$R^c$ and $R^d$ independently are selected from H, a $C_{1-20}$ alkyl group, and a $C_{1-20}$ haloalkyl group;

$R^e$ is selected from H, a $C_{1-20}$ alkyl group, a $C_{2-20}$ alkenyl group, and a $C_{1-20}$ haloalkyl group;

$R^1$, $R^{1'}$, $R^2$, and $R^{2'}$ independently are selected from H, a linear $C_{1-40}$ alkyl group, a linear $C_{2-40}$ alkenyl group, and a linear $C_{1-40}$ haloalkyl group;

m is selected from 0, 1, 2, 3, and 4; and n is selected from 0, 1, 2, 3, 4, 5, 6, 7, and 8.

In some embodiments, the present compounds can be represented by formula II:

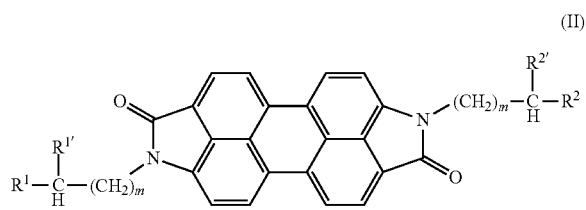

(II)

wherein $R^1$, $R^{1'}$, $R^2$, and $R^{2'}$ independently are selected from a linear $C_{1-40}$ alkyl group, a linear $C_{2-40}$ alkenyl group, and a linear $C_{1-40}$ haloalkyl group; and m are as defined herein. For example, m can be 0, 1 or 2, and accordingly, certain embodiments of the present compounds can be represented by formula IIa, IIb, or IIc:

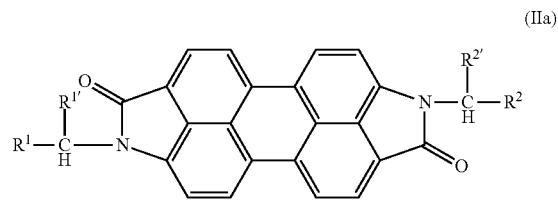

(IIa)

-continued

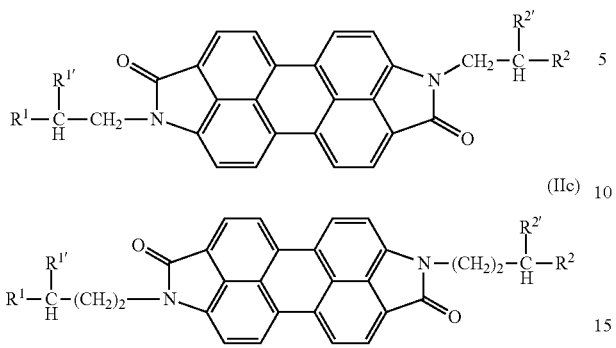

(IIb)

(IIc)

In other embodiments, the present compounds can be represented by formula I-2:

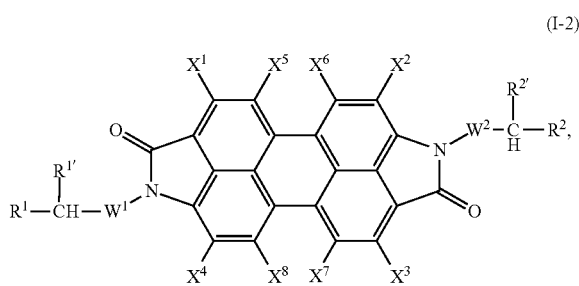

(I-2)

wherein:
$W^1$ and $W^2$ independently are selected from —$(CR^aR^b)_m$—, —$(SiR^cR^d)$—, and Ar;
$X^1$, $X^2$, $X^3$, $X^4$, $X^5$, $X^6$, $X^7$, and $X^8$ independently are selected from H, halogen, CN, and $OR^e$, provided at least one of $X^1$, $X^2$, $X^3$, $X^4$, $X^5$, $X^6$, $X^7$, and $X^8$ is not H;
Ar is a divalent aryl or heteroaryl group selected from phenyl, thienyl, and furyl;
$R^a$ and $R^b$ independently are selected from H, a $C_{1-20}$ alkyl group, a $C_{2-20}$ alkenyl group, and a $C_{1-20}$ haloalkyl group;
$R^c$ and $R^d$ independently are selected from H, a $C_{1-20}$ alkyl group, and a $C_{1-20}$ haloalkyl group;
$R^e$ is selected from H, a $C_{1-20}$ alkyl group, a $C_{2-20}$ alkenyl group, and a $C_{1-20}$ haloalkyl group;
$R^1$, $R^{1'}$, $R^2$, and $R^{2'}$ independently are selected from H, a linear $C_{1-40}$ alkyl group, a linear $C_{2-40}$ alkenyl group, and a linear $C_{1-40}$ haloalkyl group; and
m is selected from 0, 1, 2, 3, and 4.

In some embodiments, the present compounds can be represented by formula III-1:

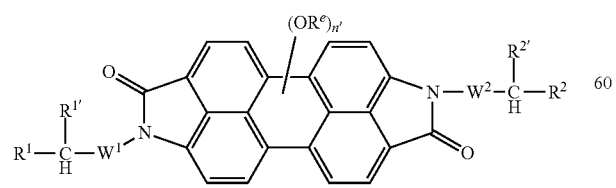

(III-1)

where $R^1$, $R^{1'}$, $R^2$, and $R^{2'}$ independently are selected from H, a linear $C_{1-40}$ alkyl group, a linear $C_{2-40}$ alkenyl group, and a linear $C_{1-40}$ haloalkyl group; n' is 1, 2, 3, 4, 5, 6, 7 or 8; and $W^1$, $W^2$, and $R^e$ are as defined herein. For example, particular embodiments may include compounds of formula III-2:

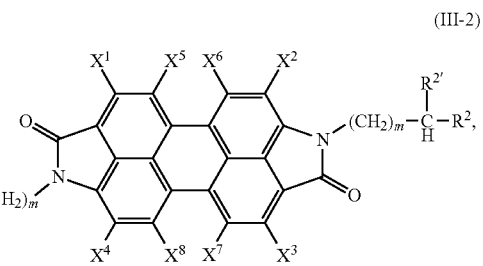

(III-2)

where $R^1$, $R^{1'}$, $R^2$, $R^{2'}$, and m are as defined herein, and at least one of $X^1$, $X^2$, $X^3$, $X^4$, $X^5$, $X^6$, $X^7$, and $X^8$ is $OR^e$, where $R^e$, for example, can be a $C_{1-20}$ alkyl group. In some embodiments, at least two of $X^1$, $X^2$, $X^3$, $X^4$, $X^5$, $X^6$, $X^7$, and $X^8$ are $OR^e$. For example, in one embodiment, $X^2$ and $X^4$ are $OR^e$, and $X^1$, $X^3$, $X^5$, $X^6$, $X^7$, and $X^8$ are H. In another embodiment, $X^6$ and $X^8$ are $OR^e$, and $X^1$, $X^2$, $X^3$, $X^4$, $X^5$, and $X^7$ are H. In yet another embodiment, $X^1$ and $X^3$ are $OR^e$, and $X^2$, $X^4$, $X^5$, $X^6$, $X^7$, and $X^8$ are H. In another embodiment, $X^5$ and $X^7$ are $OR^e$, and $X^1$, $X^2$, $X^3$, $X^4$, $X^6$, and $X^8$ are H. In yet another embodiment, $X^5$ and $X^8$ (or $X^6$ and $X^7$) are $OR^e$, and $X^1$, $X^2$, $X^3$, $X^4$, $X^6$, and $X^7$ (or $X^1$, $X^2$, $X^3$, $X^4$, $X^5$, and $X^8$) are H. In some embodiments, four of $X^1$, $X^2$, $X^3$, $X^4$, $X^5$, $X^6$, $X^7$, and $X^8$ are $OR^e$. For example, in one embodiment, $X^2$, $X^4$, $X^5$, and $X^7$ are $OR^e$, and $X^1$, $X^3$, $X^6$, and $X^8$ are H. In another embodiment, $X^5$, $X^6$, $X^7$, and $X^8$ are $OR^e$, and $X^1$, $X^2$, $X^3$, and $X^4$ are H. In yet another embodiment, $X^1$, $X^2$, $X^3$, and $X^4$ are $OR^e$, and $X^5$, $X^6$, $X^7$, and $X^8$ are H. In some embodiments, six of $X^1$, $X^2$, $X^3$, $X^4$, $X^5$, $X^6$, $X^7$, and $X^8$ are $OR^e$. For example, in one embodiment, $X^2$, $X^4$, $X^5$, $X^6$, $X^7$ and $X^8$ are $OR^e$, and $X^1$ and $X^3$ are H. In some embodiments, each of $X^1$, $X^2$, $X^3$, $X^4$, $X^5$, $X^6$, $X^7$, and $X^8$ is $OR^e$. To illustrate further, particular compounds of the present teachings can be represented by formula IIIa, IIIb, IIIc, or IIId:

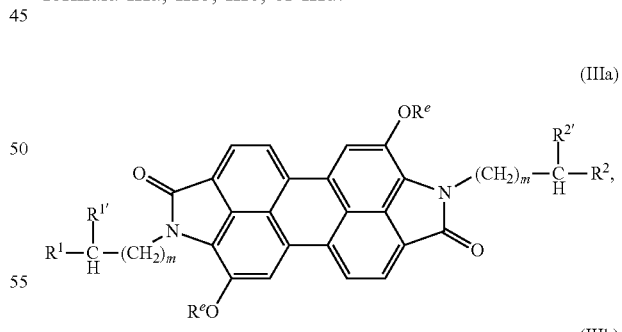

(IIIa)

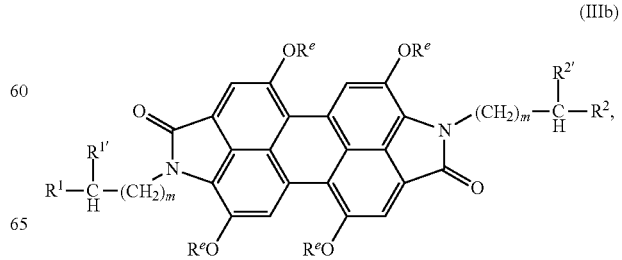

(IIIb)

-continued

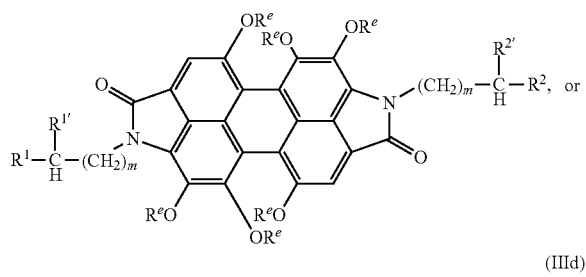
(IIIc)

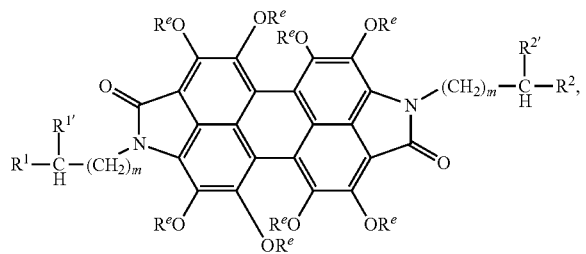
(IIId)

wherein $R^e$ is a $C_{1-20}$ alkyl group, and m is 0, 1 or 2.

In other embodiments, the present compounds can be represented by formula IV-1:

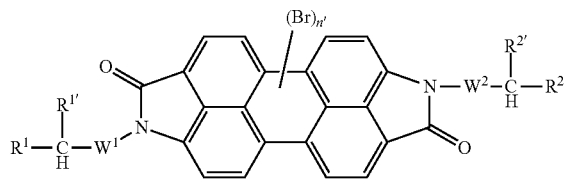
(IV-1)

where $R^1$, $R^{1'}$, $R^2$, and $R^{2'}$ independently are selected from H, a linear $C_{1-40}$ alkyl group, a linear $C_{2-40}$ alkenyl group, and a linear $C_{1-40}$ haloalkyl group; n' is 1, 2, 3, 4, 5, 6, 7 or 8; and $W^1$, $W^2$, and $R^e$ are as defined herein. For example, particular embodiments may include compounds of formula IV-2:

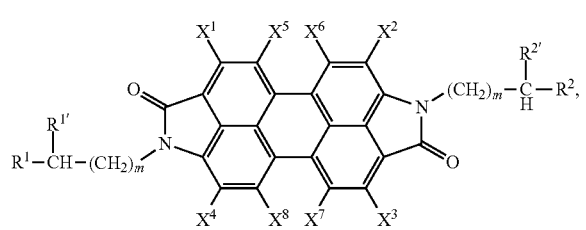
(IV-2)

where $R^1$, $R^{1'}$, $R^2$, $R^{2'}$, and m are as defined herein, and at least one of $X^1$, $X^2$, $X^3$, $X^4$, $X^5$, $X^6$, $X^7$, and $X^8$ is Br. In some embodiments, at least two of $X^1$, $X^2$, $X^3$, $X^4$, $X^5$, $X^6$, $X^7$, and $X^8$ are Br. For example, in one embodiment, $X^2$ and $X^4$ are Br, and $X^1$, $X^3$, $X^5$, $X^6$, $X^7$, and $X^8$ are H. In another embodiment, $X^6$ and $X^8$ are Br, and $X^1$, $X^2$, $X^3$, $X^4$, $X^5$, and $X^7$ are H. In yet another embodiment, $X^1$ and $X^3$ are Br, and $X^2$, $X^4$, $X^5$, $X^6$, $X^7$, and $X^8$ are H. In another embodiment, $X^5$ and $X^7$ are Br, and $X^1$, $X^2$, $X^3$, $X^4$, $X^6$, and $X^8$ are H. In yet another embodiment, $X^5$ and $X^8$ (or $X^6$ and $X^7$) are Br, and $X^1$, $X^2$)(3)(4-6 and $X^7$ (or $X^1$, $X^2$, $X^3$, $X^4$, $X^5$, and $X^8$) are H. In some embodiments, four of $X^1$, $X^2$, $X^3$, $X^4$, $X^5$, $X^6$, $X^7$, and $X^8$ are Br. For example, in one embodiment, $X^2$, $X^4$, $X^5$, and $X^7$ are Br, and $X^1$, $X^3$, $X^6$, and $X^8$ are H. In another embodiment, $X^5$, $X^6$, $X^7$, and $X^8$ are Br, and $X^1$, $X^2$, $X^3$, and $X^4$ are H. In yet another embodiment, $X^1$, $X^2$, $X^3$, and $X^4$ are Br, and $X^5$, $X^6$, $X^7$, and $X^8$ are H. In some embodiments, six of $X^1$, $X^2$, $X^3$, $X^4$, $X^5$, $X^6$, $X^7$, and $X^8$ are Br. For example, in one embodiment, $X^2$, $X^4$, $X^5$, $X^6$, $X^7$ and $X^8$ are Br, and $X^1$ and $X^3$ are H. In some embodiments, each of $X^1$, $X^2$, $X^3$, $X^4$, $X^5$, $X^6$, $X^7$, and $X^8$ is Br. To illustrate further, particular compounds of the present teachings can be represented by formula IVa, IVb, IVc, or IVd:

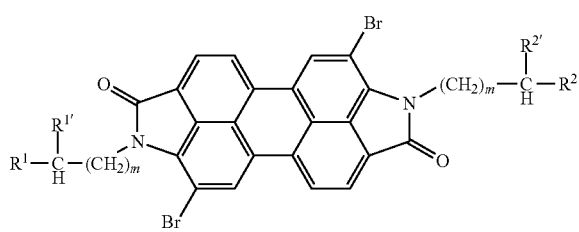
(IVa)

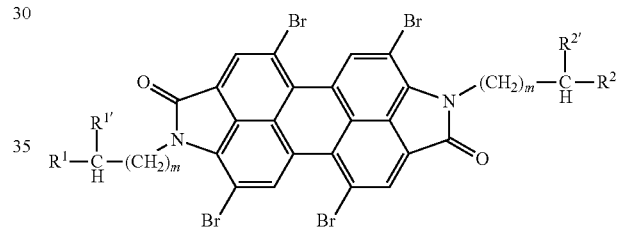
(IVb)

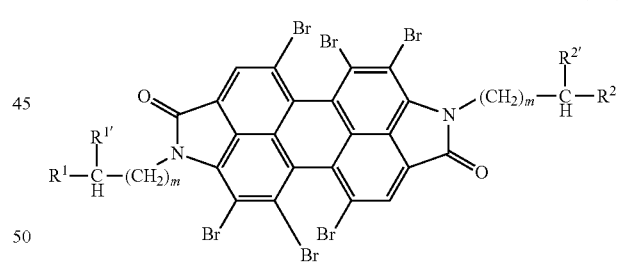
(IVc)

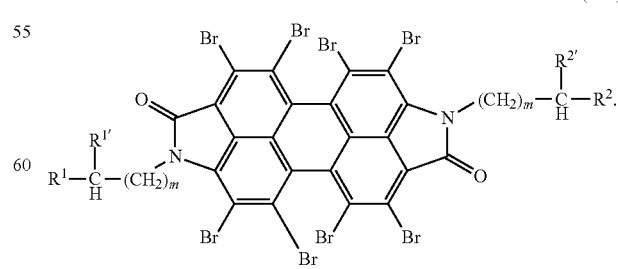
(IVd)

In yet other embodiments, the present compounds can be represented by formula V-1:

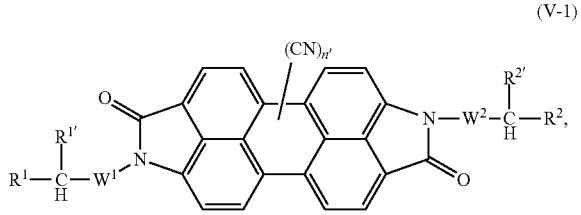

(V-1)

where $R^1$, $R^{1'}$, $R^2$, and $R^{2'}$ independently are selected from H, a linear $C_{1-40}$ alkyl group, a linear $C_{2-40}$ alkenyl group, and a linear $C_{1-40}$ haloalkyl group; n' is 1, 2, 3, 4, 5, 6, 7 or 8; and $W^1$, $W^2$, and $R^e$ are as defined herein. For example, particular embodiments may include compounds of formula V-2:

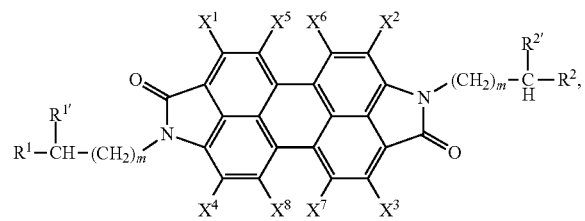

(V-2)

where $R^1$, $R^{1'}$, $R^2$, $R^{2'}$, and m are as defined herein, and at least one of $X^1$, $X^2$, $X^3$, $X^4$, $X^5$, $X^6$, $X^7$, and $X^8$ is CN. In some embodiments, at least two of $X^1$, $X^2$, $X^3$, $X^4$, $X^5$, $X^6$, $X^7$, and $X^8$ are CN. For example, in one embodiment, $X^2$ and $X^4$ are CN, and $X^1$, $X^3$, $X^5$, $X^6$, $X^7$, and $X^8$ are H. In another embodiment, $X^6$ and $X^8$ are CN, and $X^1$, $X^2$, $X^3$, $X^4$, and $X^7$ are H. In yet another embodiment, $X^1$ and $X^3$ are CN, and $X^2$, $X^4$, $X^5$, $X^6$, $X^7$, and $X^8$ are H. In another embodiment, $X^5$ and $X^7$ are CN, and $X^1$, $X^2$, $X^3$, $X^4$, $X^6$, and $X^8$ are H. In yet another embodiment, $X^5$ and $X^8$ (or $X^6$ and $X^7$) are CN, and $X^1$, $X^2$, $X^3$, $X^4$, $X^6$, and $X^7$ (or $X^1$, $X^2$, $X^3$, $X^4$, $X^5$, and $X^8$) are H. In some embodiments, four of $X^1$, $X^2$, $X^3$, $X^4$, $X^5$, $X^6$, $X^7$, and $X^8$ are CN. For example, in one embodiment, $X^2$, $X^4$, $X^5$, and $X^7$ are CN, and $X^1$, $X^3$, $X^6$, and $X^8$ are H. In another embodiment, $X^5$, $X^6$, $X^7$, and $X^8$ are CN, and $X^1$, $X^2$, $X^3$, and $X^4$ are H. In yet another embodiment, $X^1$, $X^2$, $X^3$, and $X^4$ are CN, and $X^5$, $X^6$, $X^7$, and $X^8$ are H. In some embodiments, six of $X^1$, $X^2$, $X^3$, $X^4$, $X^5$, $X^6$, $X^7$, and $X^8$ are CN. For example, in one embodiment, $X^2$, $X^4$, $X^5$, $X^6$, $X^7$ and $X^8$ are CN, and $X^1$ and $X^3$ are H. In some embodiments, each of $X^1$, $X^2$, $X^3$, $X^4$, $X^5$, $X^6$, $X^7$, and $X^8$ is CN. To illustrate further, particular compounds of the present teachings can be represented by formula Va, Vb, Vc, or Vd:

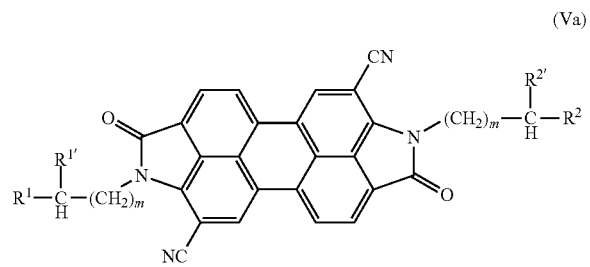

(Va)

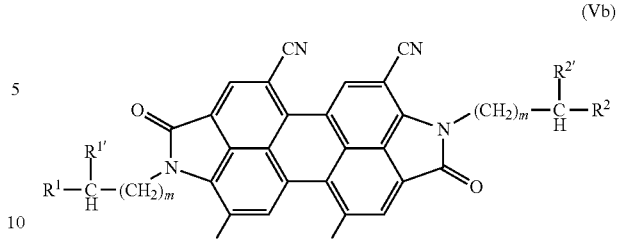

(Vb)

(Vc)

(Vd)

In any of the above embodiments, $R^1$ can be different from $R^{1'}$; and $R^2$ can be different from $R^{2'}$. For example, $R^{1'}$ and $R^{2'}$ can be selected from a linear $C_{1-6}$ alkyl group, a linear $C_{2-6}$ alkenyl group, and a linear $C_{1-6}$ haloalkyl group; whereas $R^1$ and $R^2$ can be selected from a linear $C_{3-40}$ alkyl group, a linear $C_{4-40}$ alkenyl group, and a linear $C_{3-40}$ haloalkyl group. In particular embodiments, $R^{1'}$ and $R^{2'}$ can be selected from $CH_3$, $CF_3$, $C_2H_5$, $CH_2CF_3$, $CF_2CH_3$, and $C_2F_5$; whereas $R^1$ and $R^2$ can be selected from a linear $C_{3-20}$ alkyl group, a linear $C_{4-20}$ alkenyl group, and a linear $C_{3-20}$ haloalkyl group.

Compounds of the present teachings can be prepared according to procedures described in the Examples. Alternatively, the present compounds can be prepared from commercially available starting materials, compounds known in the literature, or via other readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the polymers described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), spectrophotometry (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Various compounds according to the present teachings can have good charge transport properties and can be stable under ambient conditions ("ambient stable"), soluble in common solvents, and in turn solution-processable into various articles, structures, or devices. Accordingly, the present teachings provide for electronic devices, optical devices, and optoelectronic devices that include one or more compounds described herein as semiconductors. Examples of such electronic devices, optical devices, and optoelectronic devices include thin film semiconductors, thin film transistors (e.g., field effect transistors), photovoltaics, photodetectors, organic light emitting devices such as organic light emitting diodes (OLEDs) and organic light emitting transistors (OLETs), complementary metal oxide semiconductors (CMOSs), complementary inverters, diodes, capacitors, sensors, D flip-flops, rectifiers, and ring oscillators. In some embodiments, the present teachings provide for a thin film semiconductor including one or more compounds described herein and a field effect transistor device including the thin film semiconductor. In particular, the field effect transistor device can have a structure selected from top-gate bottom-contact structure, bottom-gate top-contact structure, top-gate top-contact structure, and bottom-gate bottom-contact structure. In certain embodiments, the field effect transistor device includes a dielectric material, wherein the dielectric material can be an organic dielectric material, an inorganic dielectric material, or a hybrid organic/inorganic dielectric material. In other embodiments, the present teachings provide for photovoltaic devices and organic light emitting devices incorporating a thin film semiconductor that includes one or more compounds described herein.

Compounds of the present teachings generally have good solubility in a variety of common solvents. Thus, various embodiments of the present compounds can be processed via inexpensive solution-phase techniques into electronic devices, optical devices, or optoelectronic devices. As used herein, a compound can be considered soluble in a solvent when at least 1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. Examples of common inorganic solvents include water and ionic liquids.

Accordingly, the present teachings further provide compositions that include one or more compounds disclosed herein dissolved or dispersed in a liquid medium, for example, an organic solvent, an inorganic solvent, or combinations thereof (e.g., a mixture of organic solvents, inorganic solvents, or organic and inorganic solvents). In some embodiments, the composition can further include one or more additives independently selected from viscosity modulators, detergents, dispersants, binding agents, compatibilizing agents, curing agents, initiators, humectants, antifoaming agents, wetting agents, pH modifiers, biocides, and bacteriostats. For example, surfactants and/or other polymers (e.g., polystyrene, polyethylene, poly-alpha-methyl styrene, polyisobutene, polypropylene, polymethylmethacrylate, and the like) can be included as a dispersant, a binding agent, a compatibilizing agent, and/or an antifoaming agent.

Various deposition techniques, including various solution-processing techniques, have been used with organic electronics. For example, much of the printed electronics technology has focused on inkjet printing, primarily because this technique offers greater control over feature position and multilayer registration. Inkjet printing is a noncontact process, which offers the benefits of not requiring a pre-formed master (compared to contact printing techniques), as well as digital control of ink ejection, thereby providing drop-on-demand printing. However, contact printing techniques have the key advantage of being well-suited for very fast roll-to-roll processing. Exemplary contact printing techniques include screen-printing, gravure, offset, flexo, and microcontact printing. Other solution processing techniques include, for example, spin-coating, spray-coating, drop-casting, zone casting, dip coating, and blade coating.

The present compounds can exhibit versatility in their processing. Formulations including the present compounds can be printable via different types of printing techniques including gravure printing, flexographic printing, and inkjet printing, providing smooth and uniform films that allow, for example, the formation of a pinhole-free dielectric film thereon, and consequently, the fabrication of all-printed devices.

The present teachings, therefore, further provide methods of preparing a semiconductor material. The methods can include preparing a composition that includes one or more compounds disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes one or more compounds disclosed herein. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin-coating, spray-coating, drop-casting, zone casting, dip coating, blade coating, or spraying. More expensive processes such as vapor deposition also can be used.

The present teachings further provide articles of manufacture, for example, composites that include a thin film semiconductor of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), self-assembled superlattice/self-assembled nanodielectric (SAS/SAND) materials (e.g., as described in Yoon, M-H. et al., PNAS, 102 (13): 4678-4682 (2005), the entire disclosure of which is incorporated by reference herein), as well as hybrid organic/inorganic dielectric materials (e.g., as described in U.S. Pat. No. 7,678,463, the entire disclosure of which is incorporated by reference herein). In some embodiments, the dielectric component can include the crosslinked polymer blends described in U.S. Pat. No. 7,605,394, the entire disclosure of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANT), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Other articles of manufacture in which compounds of the present teachings are useful are photovoltaics or solar cells. Particularly, compounds of the present teachings can exhibit broad optical absorption and/or a tuned redox properties and bulk carrier mobilities, making them desirable for such applications. For example, the compounds described herein can be used as a donor (p-type) semiconductor (for example, when X is absent or an electron-donating group such as $OR^e$) in a photovoltaic design, which includes an adjacent n-type semiconductor material that forms a p-n junction. The p-type semiconductor and the n-type semiconductor can be prepared as a semiconductor blend, which is formed into a thin film as the active layer (for light absorption and charge transfer) in the solar cell. Exploitation of compounds of the present teachings in such devices is within the knowledge of a skilled artisan.

FIG. 1 illustrates the device structure of a representative thin-film transistor, a representative bulk-heterojunction solar cell, and a representative light-emitting diode. As shown, typical thin-film transistors generally include a semiconductor layer which includes a channel layer defined by a pair of source and drain electrodes, a gate electrode (which can be deposited on a substrate, not shown), and a dielectric layer to insulate the semiconductor layer from the gate electrode. One or more compounds according to the present teachings can be incorporated into the semiconductor layer.

In certain embodiments, OTFT devices can be fabricated with one or more compounds disclosed herein on doped silicon substrates, using $SiO_2$ as the dielectric. In other embodiments, OTFT devices can be fabricated with one or more compounds disclosed herein on plastic foils, using polymers as the dielectric. In particular embodiments, the active semiconducting layer which incorporates one or more compounds disclosed herein can be deposited at room temperature or at an elevated temperature. In other embodiments, the active semiconducting layer which incorporates one or more compounds disclosed herein can be applied by spin-coating or printing as described herein. Gate and source/drain contacts can be made of Au, other metals, or conducting polymers and deposited by vapor-deposition and/or printing. A plurality of OTFT devices according to the present teachings can be printed on a flexible substrate and arranged into a flexible backplane array used to drive an optoelectronic device that can produce images, for example, an OLED display device.

In various embodiments, a semiconducting component incorporating one or more compounds disclosed herein (e.g., when X is CN) can exhibit n-type semiconducting activity, for example, an electron mobility of $10^4$ $cm^2$/V-sec or greater and/or a current on/off ratio ($I_{on}/I_{off}$) of $10^3$ or greater.

With continued reference to FIG. 1, the present compounds can be used in a solar cell which includes an active layer positioned between an anode (e.g., ITO) and a cathode (e.g., a metal such as aluminum or calcium). For example, the solar cell can be a bulk-heterojunction solar cell in which the active layer is composed of a semiconductor blend including a donor material and an acceptor material. In certain embodiments, the present compounds can be used as the donor material in the semiconductor blend, and the acceptor material can be a fullerene compound or an n-type semiconducting polymer. The present compounds also can be used in an organic light-emitting diode which, as illustrated in FIG. 1, generally includes a substrate (not shown), a transparent anode (e.g., ITO), a cathode (e.g., a metal such as aluminum or calcium), and one or more organic layers in between the anode and the cathode which can incorporate one or more semiconducting compounds of the present teachings as hole-transporting (p-channel) and/or emissive and/or electron-transporting (n-channel) materials.

The following examples are provided to illustrate further and to facilitate the understanding of the present teachings and are not in any way intended to limit the invention.

Unless otherwise noted, all reagents were purchased from commercial sources and used without further purification. Some reagents were synthesized according to known procedures. Anhydrous tetrahydrofuran (THF) was distilled from sodium/benzophenone. Reactions were carried out under nitrogen unless otherwise noted. UV-Vis spectra were recorded on a Cary Model 1 UV-vis spectrophotometer. NMR spectra were recorded on a Varian Unity Plus 500 spectrometer ($^1$H, 500 MHz; $^{13}$C, 125 MHz).

Example 1

Synthesis of 1,7-didodecylanthra[2,1,9-cde:6,5,10-c'd'e']diindole-2,8(1H,7H)dione (11)

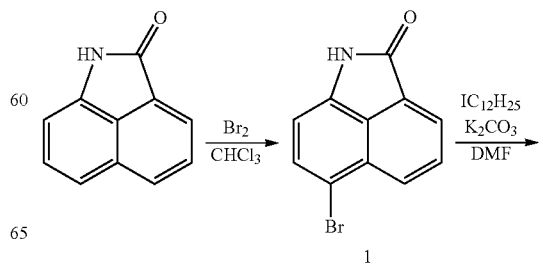

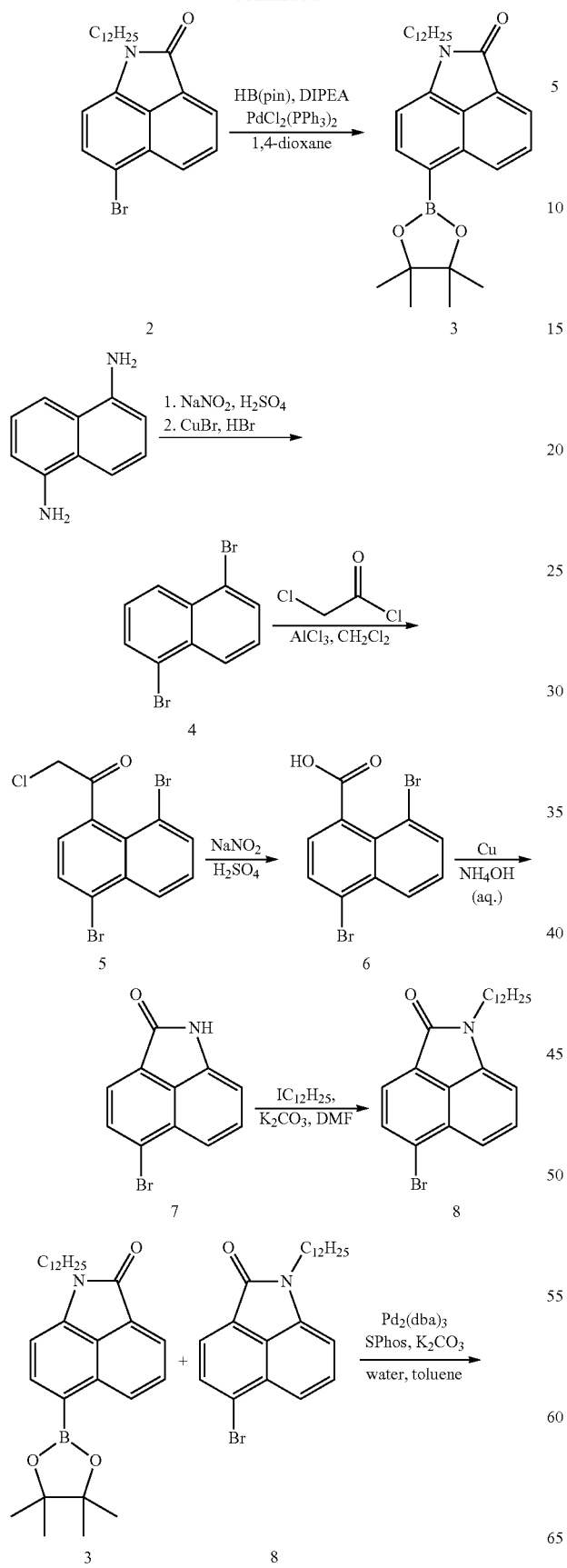
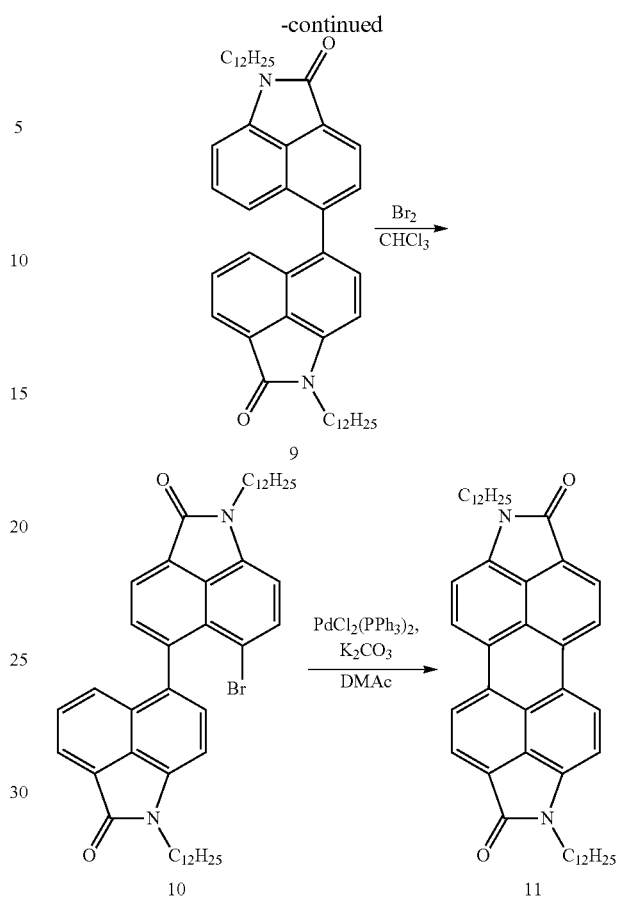

6-Bromobenz[cd]indol-2(1H)-one (1) was synthesized according to the procedures described in U.S. Pat. No. 6,667,393, but with the following modifications. Specifically, a 500-mL Schlenk flask was charged with benz[cd]indol-2(1H)-one (4.98 g, 29.4 mmol, 1.00 equiv.) and chloroform (120 mL). The suspension was heated to dissolve the starting material and then cooled to 0° C. Bromine (1.51 mL, 29.4 mmol, 1.00 equiv.) was added over five minutes. The suspension was left to warm to room temperature and stirred for 64 hours. The resulting thick suspension was diluted with hexanes (100 mL) and filtered to collect the orange crude solid. Recrystallization from toluene (600 mL) gave the title compound as a yellow solid (4.93 g, 68%). $^1$H NMR (400 MHz, CDCl$_3$) d 8.20 (1H, d, J=8.3 Hz), 8.12 (1H, d, J=7.0 Hz), 7.84 (1H, dd, J=8.2, 7.1 Hz), 7.70 (1H, m), 7.67 (1H, d, J=7.5 Hz), 6.83 (1H, d, J=7.5 Hz).

1-Dodecyl-6-bromobenz[cd]indol-2(1H)-one (2) was synthesized according to the procedures described in U.S. Pat. No. 6,667,393, but with the following modifications. Specifically, a 500-mL Schlenk flask was charged with 6-bromobenz[cd]indol-2(1H)-one (1, 4.85 g, 19.6 mmol, 1.0 equiv.), potassium carbonate (27.0 g, 196 mmol, 10 equiv.), DMF (200 mL) and 1-iodododecane (8.69 g, 29.3 mmol, 1.5 equiv.). The reaction vessel was placed in an oil bath set at 65° C. and stirred for 24 hours. The mixture was cooled to room temperature and diluted with water (200 mL) and ether (500 mL). The organic layer was separated and washed with water (2×300 mL) and brine (200 mL), and then was dried with MgSO$_4$. The solution was concentrated, and the residue was subjected to recrystallization from methanol (400 mL) to give the title compound as yellow needle-like crystals (7.22 g, 88%). $^1$H NMR (400 MHz, CDCl$_3$) d 8.15 (1H, d, J=8.3 Hz), 8.09 (1H, d, J=7.0 Hz), 7.84-7.76 (1H, m), 7.66 (1H, d, J=7.5 Hz), 6.76 (1H, d, J=7.5 Hz), 3.89 (2H, t, J=7.2 Hz), 1.82-1.70 (2H, m), 1.43-1.16 (18H, m), 0.87 (3H, t, J=6.8 Hz).

1-Dodecyl-6-(4,4,5,5-tetramethyl-1,3,2-dioxaborolan-2-yl)benz[cd]indol-2(1H)-one (3): A 500-ml Schlenk flask was charged with 1-dodecyl-6-bromobenz[cd]indol-2(1H)-one (2, 4.00 g, 9.61 mmol, 1.00 equiv), 1,4-dioxane (80 mL), diisopropylethylamine (4.5 mL), 4,4,5,5-tetramethyl-1,3,2-dioxaborolane (also known as pinacolborane or HB(pin), 2.1 mL, 14 mmol, 1.5 equiv.) and PdCl$_2$(PPh$_3$)$_2$ (202 mg, 0.288 mmol, 3 mol %). The reaction vessel was placed in a 95° C. heat bath and stirred at this temperature for 16 hours. The reaction mixture was diluted with water (250 mL) and ether (350 mL). The organic layer was washed with brine, dried with MgSO$_4$ and concentrated. Purification by silica gel column chromatography, using a gradient of 9:1 to 5:1 hexanes-EtOAc as the eluent, gave the title compound as a viscous yellow liquid (3.442 g, 77%). $^1$H NMR (400 MHz, CDCl$_3$) d 8.75 (1H, d, J=8.2 Hz), 8.05 (2H, td, J=12.8, 5.1 Hz), 7.73 (1H, dd, J=8.2, 7.0 Hz), 6.91 (1H, d, J=7.2 Hz), 3.95-3.86 (2H, m), 1.77 (2H, td, J=14.8, 7.5 Hz), 1.45-1.17 (27H, m), 0.87 (3H, t, J=6.9 Hz).

1,5-Dibromonaphthalene (4): A 2.0 L 3-neck round bottom flask was charged with water (500 mL) and concentrated sulfuric acid (33 mL). The solution was cooled to 0° C. 1,5-Diaminonaphthalene (20.0 g, 126 mmol, 1.00 equiv.) was then added. A separately prepared 0° C. solution of sodium nitrite (21.8 g, 316 mmol, 2.50 equiv.) was then added over 10 minutes. The brown mixture was stirred at 0° C. for 90 minutes, and then was carefully poured over 5 minutes into a 3.0 L 3-neck flask containing a 0° C. solution of hydrogen bromide (48 wt. % in water, 400 mL) and copper(I) bromide (50.0 g, 349 mmol, 2.76 equiv.). The mixture immediately began to evolve gas. The reaction mixture was stirred at 0° C. for 30 minutes before warming to room temperature (using a heating mantle), and was kept at room temperature for 30 minutes. The temperature was then increased to 70° C. and the reaction was kept at this temperature until gas evolution ceased (about 1 hour). After cooling to room temperature, the mixture was filtered and the crude solid was washed with water and dried. This was then diluted with hexane (approximately 2 L), stirred and sonicated. The mixture was filtered through a silica gel column, which was rinsed with additional hexane. The filtrate was concentrated to a colorless solid (22.33 g, 62%). $^1$H NMR (400 MHz, CDCl$_3$) d 8.26 (1H, d, J=8.5 Hz), 7.85 (1H, d, J=7.5 Hz), 7.43 (1H, t, J=6.9 Hz)

2-Chloro-1-(4,8-dibromo-1-naphthalenyl)ethanone (5) was synthesized according to a the procedures described in Bystritskii, G. I. et al., *Russian Journal of Organic Chemistry*, 9: 1067 (1973), but with the following modifications. Specifically, a 500-mL 3-neck round bottom flask was charged with 1,5-dibromonaphthalene (4, 5.00 g, 17.5 mmol, 1.00 equiv.) and 1,2-dichloroethane (40 mL). The solution was cooled to 0° C., and chloroacetyl chloride (3.0 mL, 38 mmol, 2.2 equiv.) and aluminum chloride (6.00 g, 45.0 mmol, 2.57 equiv.) were added. The reaction mixture was left to stir overnight while warming to room temperature. The reaction mixture was cautiously diluted with water (50 mL). The organic layer was washed with brine, dried with MgSO$_4$ and concentrated. Recrystallization from ethanol gave the title compound as colorless needle-like crystals (5.148 g, 81%). $^1$H NMR (400 MHz, CDCl$_3$) d 8.41 (1H, dd, J=8.6, 1.1 Hz), 7.94 (1H, dd, J=7.5, 1.1 Hz), 7.87 (1H, d, J=7.7 Hz), 7.52 (1H, dd, J=8.5, 7.5 Hz), 7.29 (1H, d, J=7.7 Hz), 4.62 (2H, b).

4,8-Dibromo-1-naphthalenecarboxylic acid (6) was synthesized according to the procedures described in Ito, S. et al., *Org. Lett.*, 15: 3110 (2013). Specifically, a 500-mL three-neck round bottom flask was charged with 2-chloro-1-(4,8-dibromo-1-naphthalenyl) ethanone (5, 11.1 g, 30.6 mmol, 1.00 equiv.), sulfuric acid (120 mL) and sodium nitrite (2.16 g, 31.3 mmol, 1.02 equiv.). The reaction vessel was placed in a 65° C. heat bath and stirred for 45 minutes. The reaction mixture was poured into cold water (500 mL) and filtered. The solid thus obtained was added to a 10% sodium carbonate solution (1 L) and stirred for 30 minutes at room temperature. The mixture was filtered, and the filtrate was cautiously acidified with hydrochloric acid while stirring. The solid was collected by filtration and washed with water to give the title compound as a beige solid (4.77 g, 47%). $^1$H NMR (500 MHz, CDCl$_3$) d 8.39 (1H, dd, J=8.5, 0.9 Hz), 7.98 (1H, dd, J=7.5, 0.9 Hz), 7.88 (1H, d, J=7.7 Hz), 7.65 (1H, d, J=7.7 Hz), 7.51 (1H, dd, J=10.3, 5.7 Hz).

5-Bromobenz[cd]indol-2(1H)-one (7) was synthesized according to the procedures described in Ito, S. et al., *Org. Lett.*, 15: 3110 (2013). Specifically, a 250-mL 2-neck round bottom flask was fitted with a reflux condenser and charged with 4,8-dibromo-1-naphthalenecarboxylic acid (6, 4.77 g, 14.5 mmol, 1.00 equiv), copper powder (240 mg, 3.78 mmol, 0.26 equiv.) and 28% aqueous ammonium hydroxide solution (50 mL). The flask was placed in an 80° C. heat bath and stirred 45 minutes at this temperature. Additional ammonium hydroxide solution (50 mL) was then added, and the mixture was stirred an additional 45 minutes before cooling to room temperature. The reaction mixture was poured into hydrochloric acid (1 N, 500 mL) and boiled for 10 minutes while stirring. The resulting yellow suspension was cooled to room temperature and filtered. Recrystallization from toluene gave the title compound as a yellow solid (2.27 g, 63%). $^1$H NMR (400 MHz, CDCl$_3$) d 7.96 (1H, d, J=7.4 Hz), 7.90 (1H, d, J=7.4 Hz), 7.68 (1H, d, J=8.7 Hz), 7.64-7.57 (1H, b), 7.54 (1H, dd, J=8.7, 7.2 Hz), 6.99 (1H, d, J=7.2 Hz).

1-Dodecyl-5-bromobenz[cd]indol-2(1H)-one (8) was synthesized in the same manner as 1-dodecyl-6-bromobenz [cd]indol-2(1H)-one (vide supra). The procedure executed on 2.26 g of 5-bromobenz[cd]indol-2(1H)-one (7) gave the title compound as yellow needlelike crystals (3.13 g, 83%). $^1$H NMR (400 MHz, CDCl$_3$) d 7.92 (1H, d, J=7.4 Hz), 7.87 (1H, d, J=7.4 Hz), 7.64 (1H, d, J=8.6 Hz), 7.54 (1H, dd, J=8.6, 7.0 Hz), 6.93 (1H, d, J=7.0 Hz), 3.89 (2H, t, J=7.3 Hz), 1.76 (2H, d, J=7.5 Hz), 1.42-1.18 (18H, m), 0.87 (3H, t, J=6.8 Hz).

1-Dodecyl-5-(1-dodecylbenz[cd]indol-2(1H)-one-6-yl)-benz[cd]indol-2(1H)-one (9) was synthesized using a procedure adapted from the procedures described in Ito, S. et al., *Org. Lett.*, 15: 3110 (2013). Specifically, a 100-mL Schlenk flask was charged with 1-dodecyl-6-(4,4,5,5-tetramethyl-1,3,2-dioxaborolan-2-yl)benz[cd]indol-2(1H)-one (3, 1.11 g, 2.40 mmol, 1.00 equiv.), toluene (180 mL), and water (30 mL). Nitrogen was bubbled through the mixture for 30 minutes. 1-Dodecyl-5-bromobenz[cd]indol-2(1H)-one (8, 1.00 g, 2.40 mmol, 1.00 equiv.), bis(dibenzylideneacetone)palladium(0) (138 mg, 240 µmol, 10 mol %), 2-dicyclohexylphosphino-2',6'-dimethoxybiphenyl (SPhos, 197 mg, 480 µmol, 20 mol %) and potassium carbonate (3.98 g, 28.8 mmol, 12.0 equiv.) were added. The flask was placed in a 105° C. heat bath and stirred at this temperature for 3 hours. The reaction mixture was brought to room temperature, diluted with water (300 mL) and diethyl ether (300 mL). The organic phase was washed with brine (200 mL), dried with MgSO$_4$ and concentrated. Silica gel column chromatography, eluting with 14:1 CH$_2$Cl$_2$-EtOAc, gave the title compound as a bright yellow solid (1.189 g, 74%). $^1$H NMR (400 MHz, CDCl$_3$) d 8.17 (1H, d, J=7.2 Hz), 8.11 (1H, d, J=6.9 Hz), 7.78 (2H, t, J=7.8 Hz), 7.65 (1H, dd, J=8.2, 7.0 Hz), 7.55 (1H, d, J=7.3 Hz), 7.38 (1H, dd, J=8.6, 7.0 Hz), 7.29 (1H, d, J=8.6 Hz), 7.06 (1H, d, J=7.3 Hz), 6.94 (1H, d, J=7.0 Hz), 3.98 (4H, dd, J=15.8, 7.5 Hz), 1.90-1.77 (4H, m), 1.50-1.18 (36H, m), 0.87 (6H, td, J=6.9, 3.3 Hz).

1-Dodecyl-5-(1-dodecylbenz[cd]indol-2(1H)-one-6-yl)-6-bromobenz[cd]indol-2(1H)-one (10): A 100-mL Schlenk flask was charged with 1-dodecyl-5-(1-dodecylbenz[cd]indol-2(1H)-one-6-yl)-benz[cd]indol-2(1H)-one (9, 1.05 g, 1.56 mmol, 1.00 equiv.) and chloroform (30 mL). The solution was cooled to 0° C. and bromine (80 µL, 1.6 mmol, 1.0 equiv.) was added. The ice/water bath was left in place and the reaction mixture was left to warm to room temperature while stirring for 64 hours. The reaction mixture was diluted with water (40 mL). The aqueous layer was extracted with CH$_2$Cl$_2$ (30 mL), and the organic layers were combined, dried with MgSO$_4$ and concentrated. The title compound was collected by trituration from methanol as a bright yellow solid (1.05 g, 90%). $^1$H NMR (400 MHz, CDCl$_3$) d 8.16 (1H, d, J=7.1 Hz), 8.07 (1H, d, J=6.9 Hz), 7.73 (1H, d, J=7.1 Hz), 7.64 (1H, d, J=7.6 Hz), 7.59 (1H, dd, J=8.2, 7.0 Hz), 7.43 (1H, d, J=8.2 Hz), 7.40 (1H, d, J=7.2 Hz), 7.00 (1H, d, J=7.2 Hz), 6.81 (1H, d, J=7.6 Hz), 4.07-3.89 (4H, m), 1.93-1.74 (4H, m), 1.52-1.18 (36H, m), 0.88 (6H, dt, J=7.0, 6.8, 2.2 Hz).

1,7-Didodecylanthra[2,1,9-cde:6,5,10-c'd'e']diindole-2,8 (1H,7H)dione (11): A 15-mL Schlenk tube was charged with 1-dodecyl-5-(1-dodecylbenz[cd]indol-2(1H)-one-6-yl)-6-bromobenz[cd]indol-2(1H)-one (10, 131 mg, 174 µmol, 1.00 equiv), N,N-dimethylacetamide (4.5 mL), potassium carbonate (granular, 36 mg, 260 µmol, 1.5 equiv.), and palladium bis(triphenylphosphine)palladium(II) dichloride (24 mg, 35 µmol, 20 mol %). The reaction tube was placed in a 100° C. heat bath and stirred at this temperature for 16 hours. The reaction mixture was cooled to room temperature and diluted with water (20 mL) and chloroform (20 mL) and stirred. The biphasic mixture was further diluted with water and chloroform, and the aqueous layer was extracted with chloroform (3×80 mL). The organic layer (separated using a phase separator membrane) was dried with MgSO$_4$ and concentrated. The residue was loaded in chloroform onto a silica gel column and eluted with a mixture of 2% ethyl acetate in chloroform. The fractions with a strong pink/orange color were combined and concentrated to give a mixture of the title compound with an impurity presumed to be the 5-membered ring isomer. Recrystallization was performed as follows: the mixture was dissolved in hot hexanes, and upon cooling a precipitate formed. This suspension was filtered through a syringe filter, which was washed with additional hexanes. Chloroform was then passed though the syringe filter to dissolve the solids, and the bright pink filtrate was concentrated to afford the title compound as a dark solid (21 mg, 8.2%). $^1$H NMR (400 MHz, CDCl$_3$) d 8.16 (2H, d, J=7.66 Hz), 8.07 (2H, d, J=7.70 Hz), 8.02 (2H, d, J=7.60 Hz), 6.90 (2H, d, J=7.64 Hz), 3.90 (4H, t, J=7.24 Hz), 1.83-1.72 (4H, m), 1.44-1.14 (36H, m), 0.84 (6H, m). m.p. 240-242° C.

Figure 2:
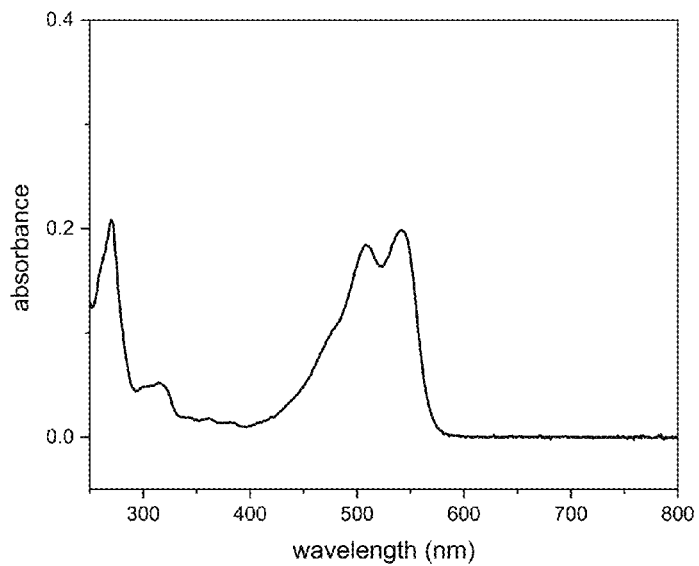
FIG. 2 shows the UV-Vis absorption in CHCl3 for compound 11.
Figure 3:
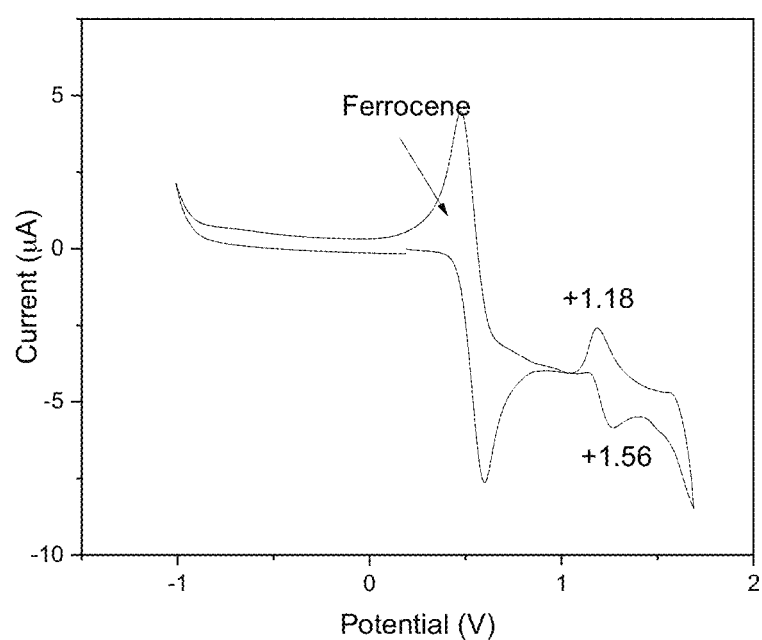
FIG. 3 shows cyclic voltammograms of compound 11 in $CH_2Cl_2$. Ferrocene was used as an internal standard with its peak adjusted to 0.54 V.

FIGS. 2 and 3 show the UV-vis spectrum and cyclic voltammogram of the title compound.

Alternative Synthetic Routes to Alkylated Compounds

Alkylated compounds according to the present teachings can be synthesized from intermediate 9 (where R can be C$_{12}$H$_{25}$ or other W$^1$CHR$^1$R$^1$'/W$^2$CHR$^2$R$^2$' groups as defined herein) according to the proposed synthetic schemes below:

Scheme 2

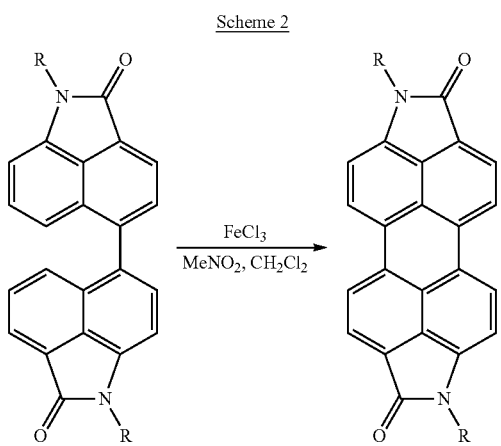

Scheme 3

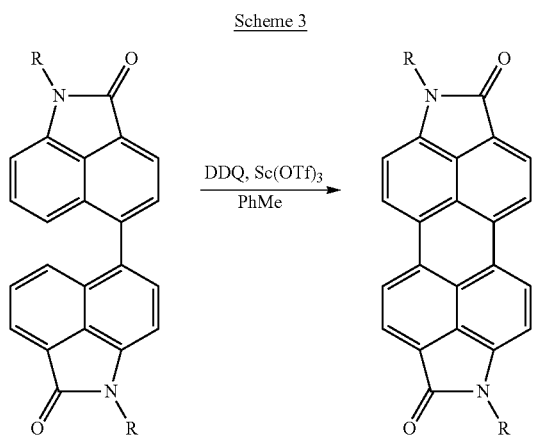

Scheme 4

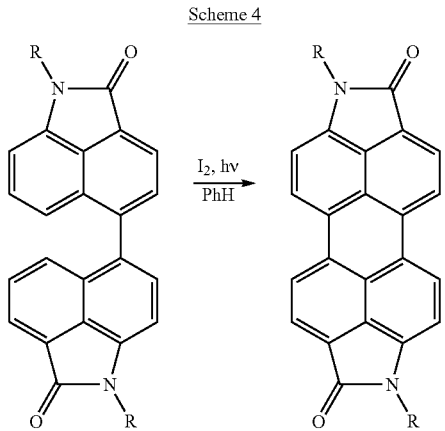

Scheme 5

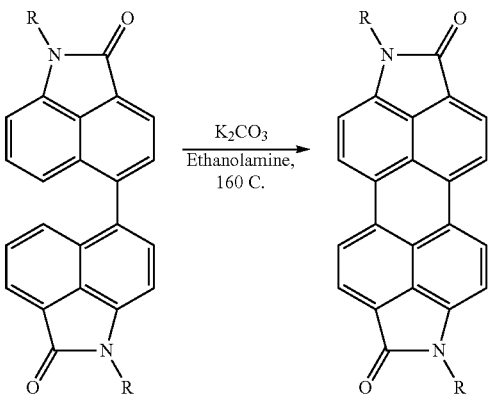

Scheme 8

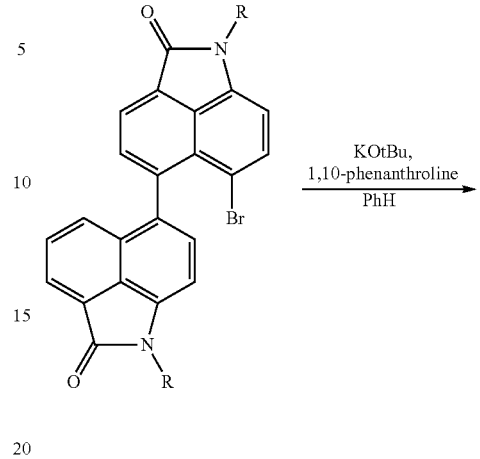

Scheme 6

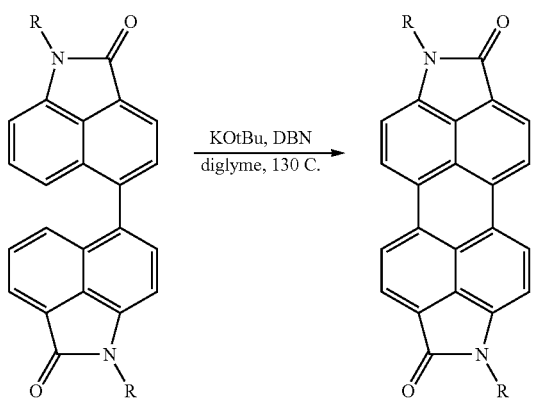

Additionally, alkylated compounds according to the present teachings can be synthesized from intermediate 10 (where R can be $C_{12}H_{25}$ or other $W^1CHR^1R^{1'}/W^2CHR^2R^{2'}$ groups as defined herein) according to the proposed synthetic schemes below:

Scheme 7

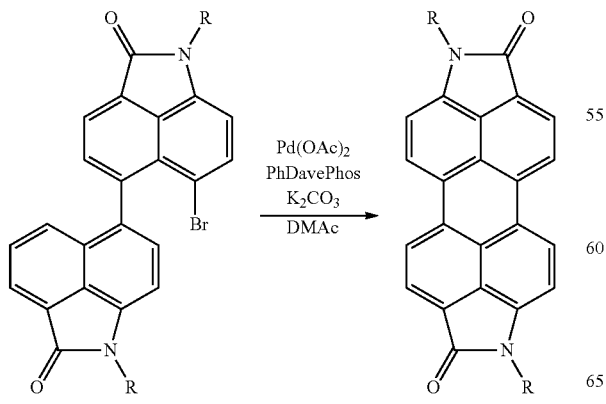

Selective Bromination and Cyanation of Perylene Core

Bromo-substituted compounds according to the present teachings can be prepared according to the proposed synthetic schemes below:

Scheme 9

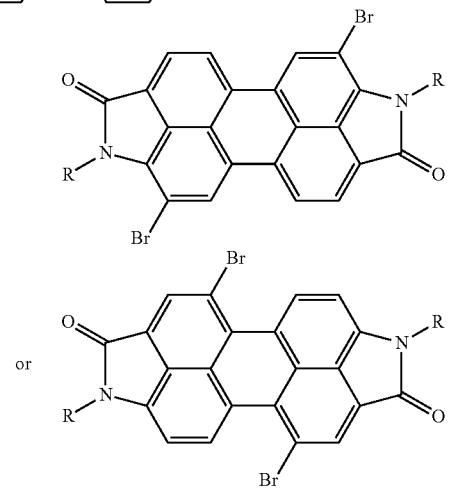

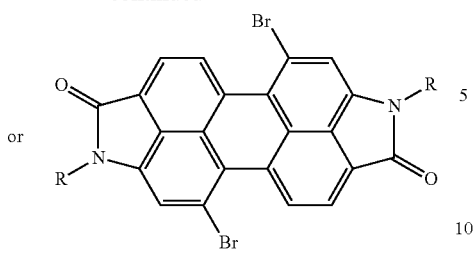
or
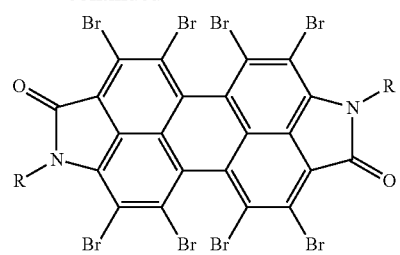
The bromo-substituted compounds can then be cyanated according to the proposed synthetic schemes below:
Scheme 10
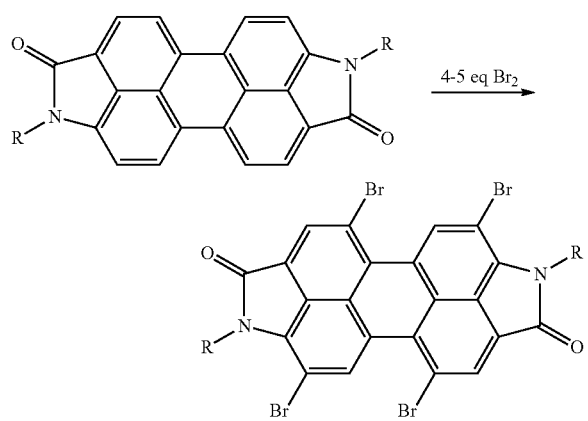
Scheme 13
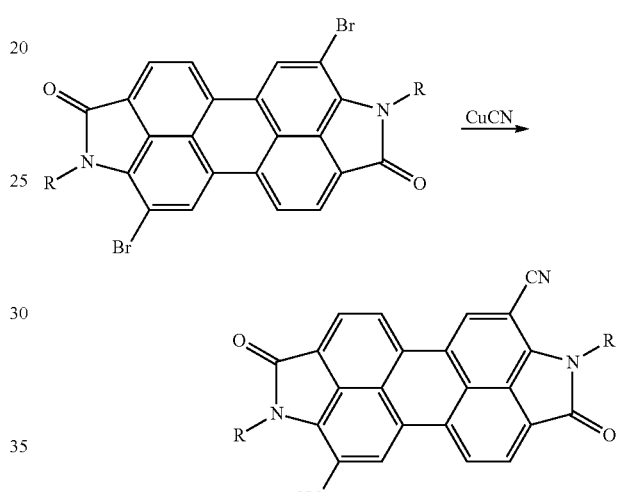
Scheme 11
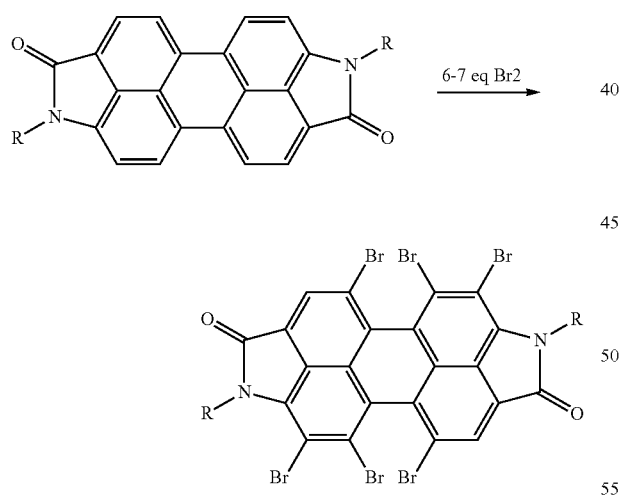
Scheme 12
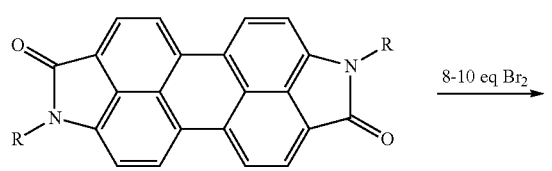
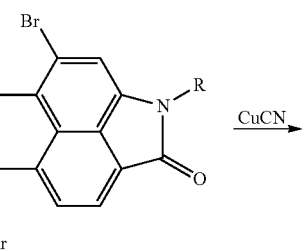

-continued

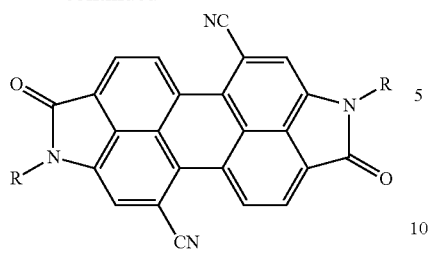

Scheme 14

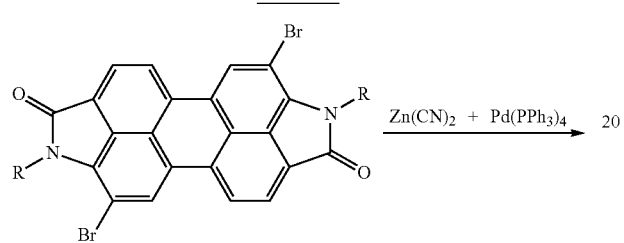

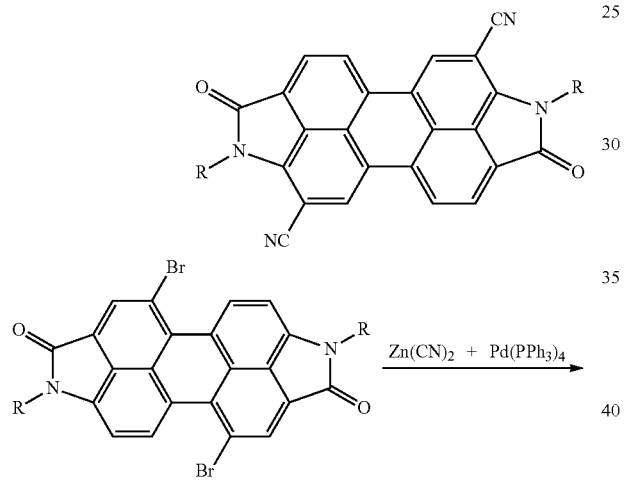

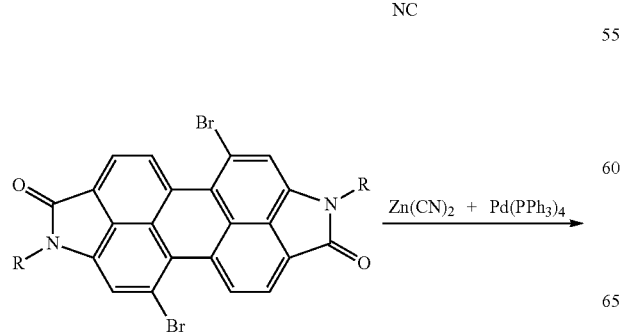

-continued

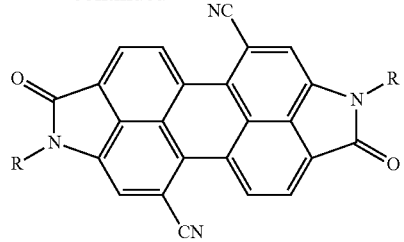

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. A compound of formula:

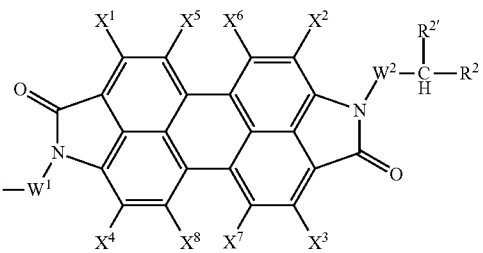

wherein:

$W^1$ and $W^2$ independently are selected from the group consisting of —$(CR^aR^b)_m$—, —$(SiR^cR^d)$—, and Ar;

$X^1$, $X^2$, $X^3$, $X^4$, $X^5$, $X^6$, $X^7$, and $X^8$ independently are selected from the group consisting of H, halogen, CN, and $OR^e$, provided at least one of $X^1$, $X^2$, $X^3$, $X^4$, $X^5$, $X^6$, $X^7$, and $X^8$ is not H;

Ar is a divalent aryl or heteroaryl group selected from the group consisting of phenyl, thienyl, and furyl;

$R^a$ and $R^b$ independently are selected from the group consisting of H, a $C_{1-20}$ alkyl group, a $C_{2-20}$ alkenyl group, and a $C_{1-20}$ haloalkyl group;

$R^c$ and $R^d$ independently are selected from the group consisting of H, a $C_{1-20}$ alkyl group, and a $C_{1-20}$ haloalkyl group;

$R^e$ is selected from the group consisting of H, a $C_{1-20}$ alkyl group, a $C_{2-20}$ alkenyl group, and a $C_{1-20}$ haloalkyl group;

$R^1$, $R^{1'}$, $R^2$, and $R^{2'}$ independently are selected from the group consisting of H, a linear $C_{1-40}$ alkyl group, a linear $C_{2-40}$ alkenyl group, and a linear $C_{1-40}$ haloalkyl group; and m is 0, 1, 2, 3, or 4.

2. The compound of claim 1, wherein the compound is represented by the formula:

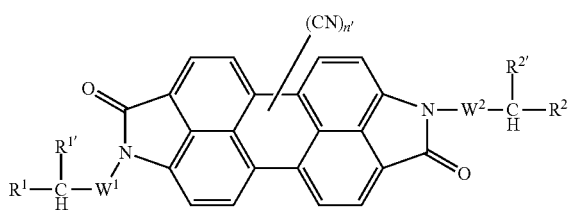

wherein n' is 2, 4, 6 or 8; and $R^1$, $R^{1'}$, $R^2$, $R^{2'}$, $W^1$, and $W^2$ are as defined in claim 1.

3. The compound of claim 1, wherein the compound is represented by the formula:

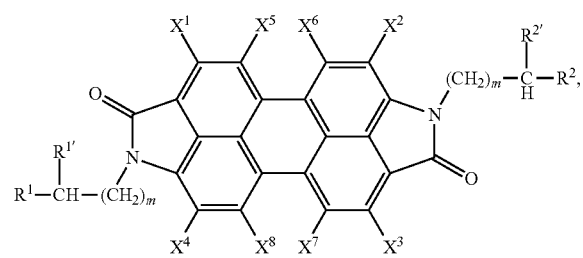

wherein two of $X^1$, $X^2$, $X^3$, $X^4$, $X^5$, $X^6$, and $X^8$ are CN, and the other six of $X^1$, $X^2$, $X^3$, $X^4$, $X^5$, $X^6$, $X^7$, and $X^8$ are H.

4. The compound of claim 3, wherein $X^2$ and $X^4$ are CN, and $X^1$, $X^3$, $X^5$, $X^6$, $X^7$, and $X^8$ are H.

5. The compound of claim 3, wherein $X^6$ and $X^8$ are CN, and $X^1$, $X^2$, $X^3$, $X^4$, $X^5$, and $X^7$ are H.

6. The compound of claim 3, wherein $X^1$ and $X^3$ are CN, and $X^2$, $X^4$, $X^5$, $X^6$, $X^7$, and $X^8$ are H.

7. The compound of claim 3, wherein $X^5$ and $X^7$ are CN, and $X^1$, $X^2$, $X^3$, $X^4$, $X^6$, and $X^8$ are H.

8. The compound of claim 3, wherein $X^5$ and $X^8$ are CN, and $X^1$, $X^2$, $X^3$, $X^4$, $X^6$, and $X^7$ are H.

9. The compound of claim 1, wherein the compound is represented by a formula selected from the group consisting of:

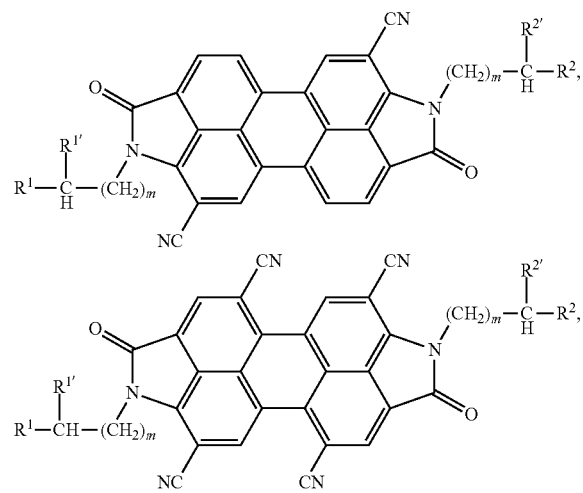

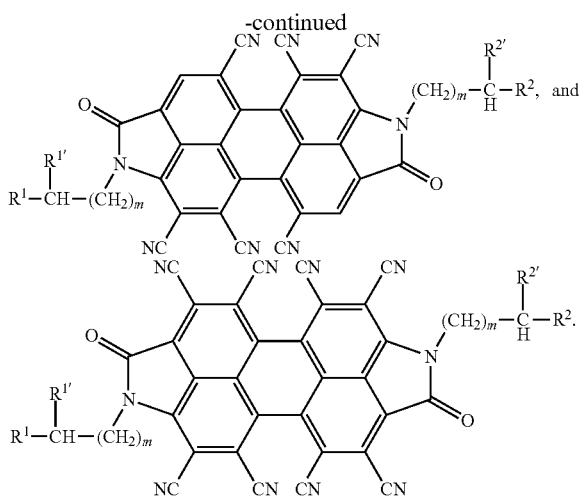

10. The compound of claim 1, wherein $R^1$ is different from $R^{1'}$, and $R^2$ is different from $R^{2'}$.

11. The compound of claim 1, wherein $R^{1'}$ and $R^{2'}$ are selected from the group consisting of consisting of a linear $C_{1-6}$ alkyl group, a linear $C_{2-6}$ alkenyl group, and a linear $C_{1-6}$ haloalkyl group; and $R^1$ and $R^2$ are selected from the group consisting of a linear $C_{3-40}$ alkyl group, a linear $C_{4-40}$ alkenyl group, and a linear $C_{3-40}$ haloalkyl group.

12. The compound of claim 1, wherein $R^{1'}$ and $R^{2'}$ are selected from the group consisting of $CH_3$, $CF_3$, $C_2H_5$, $CH_2CF_3$, $CF_2CH_3$, and $C_2F_5$; and $R^1$ and $R^2$ are selected from the group consisting of a linear $C_{3-20}$ alkyl group, a linear $C_{4-20}$ alkenyl group, and a linear $C_{3-20}$ haloalkyl group.

13. A thin film semiconductor comprising a compound of claim 1.

14. A composite comprising a substrate and the thin film semiconductor of claim 13 deposited on the substrate.

15. An electronic device, an optical device, or an optoelectronic device comprising the thin film semiconductor of claim 13.

16. A field effect transistor device comprising a source electrode, a drain electrode, a gate electrode, and the thin film semiconductor of claim 13 in contact with a dielectric material.

17. The device of claim 16, wherein the field effect transistor has a structure selected from the group consisting of a top-gate bottom-contact structure, a bottom-gate top-contact structure, a top-gate top-contact structure, and a bottom-gate bottom-contact structure.

18. The device of claim 16, wherein the dielectric material comprises an organic dielectric material.

19. The device of claim 16, wherein the dielectric material comprises an inorganic dielectric material or a hybrid organic/inorganic dielectric material.

20. An optoelectronic device for producing an image, the optoelectronic device comprising a plurality of field effect transistors interconnected to each other and deposited on a substrate, such field effect transistors each comprising a thin film semiconductor comprising a compound of claim 1, a source electrode, a drain electrode, a gate electrode, and a dielectric material.

* * * * *